United States Patent
Voorhees, Jr. et al.

(10) Patent No.: US 7,556,617 B2
(45) Date of Patent: Jul. 7, 2009

(54) CATHETER SAFETY NEEDLE

(75) Inventors: Earl W. Voorhees, Jr., Warrington, PA (US); John Stephens, Perkiomenville, PA (US); Kenneth J. Chesnin, Philadelphia, PA (US)

(73) Assignee: Medical Components, Inc., Harleysville, PA (US)

( * ) Notice: Subject to any disclaimer, the term of this patent is extended or adjusted under 35 U.S.C. 154(b) by 713 days.

(21) Appl. No.: 11/061,922

(22) Filed: Feb. 18, 2005

(65) Prior Publication Data

US 2005/0192545 A1 Sep. 1, 2005

Related U.S. Application Data

(60) Provisional application No. 60/548,427, filed on Feb. 26, 2004.

(51) Int. Cl.
*A61M 5/178* (2006.01)
(52) U.S. Cl. .............. 604/164.01; 604/164.08; 604/162; 604/198; 604/263
(58) Field of Classification Search .......... 604/198, 604/263, 192, 171, 164.01, 164.08, 162
See application file for complete search history.

(56) References Cited

U.S. PATENT DOCUMENTS

| 4,170,993 | A | * | 10/1979 | Alvarez | 604/180 |
|---|---|---|---|---|---|
| 4,917,679 | A | * | 4/1990 | Kronner | 604/198 |
| 5,169,391 | A | | 12/1992 | Vogel | |
| 5,273,540 | A | | 12/1993 | Luther et al. | |
| 5,279,581 | A | | 1/1994 | Firth et al. | |
| 5,312,359 | A | | 5/1994 | Wallace | |

(Continued)

OTHER PUBLICATIONS

Product Brochure: "AV fistula Needles with MasterGuard® Anti-Stick Needle Protector"; Medisystems Hemo*DYNAMIC* Devices™; Copyright 2002; ADV004 May 2, 2002; USA.

(Continued)

*Primary Examiner*—Nicholas D Lucchesi
*Assistant Examiner*—Laura A Bouchelle
(74) *Attorney, Agent, or Firm*—Anton P. Ness; Fox Rothschild LLP

(57) ABSTRACT

A catheter insertion needle assembly (100) including a generally elongated body (110), a slider assembly (120), and a needle housing (126) with a needle (130). The elongated body has a proximal end (114) and a distal end (112), a needle guard (140) disposed at the distal end of the body in a needle guard plane, a first or distal locking member (150), and a second or proximal locking member (118). The slider assembly (120) includes a slider (122) that is slidably disposed on the body (110) Needle (130) has a distal tip (134) and a cannulating portion (132) extending therethrough. A first locking tab (121) is releasably engageable with the first locking member (150) and a second locking portion is lockably engageable with the second locking member (118). The first locking tab (121) is releasable from the first locking member to allow the slider (122) to slide between a distal position relative to the body (110) wherein the tip (134) extends distally of the needle guard (140), and a proximal position relative to the body wherein the tip (134) is disposed within the needle guard plane. When the slider (122) is disposed at the proximal position, the second locking portion engages the second locking member (118) to preclude the slider (122) from sliding distally relative to the body (110).

19 Claims, 5 Drawing Sheets

U.S. PATENT DOCUMENTS

| | | |
|---|---|---|
| 5,501,672 A | 3/1996 | Firth et al. |
| 5,562,637 A | 10/1996 | Utterberg |
| 5,651,772 A | 7/1997 | Arnett |
| 5,688,249 A * | 11/1997 | Chang et al. ............ 604/198 |
| 5,795,339 A | 8/1998 | Erskine |
| 5,951,523 A | 9/1999 | Österlind et al. |
| 5,951,529 A | 9/1999 | Utterberg |
| RE36,885 E | 9/2000 | Blecher et al. |
| 6,159,184 A | 12/2000 | Perez et al. |
| 6,213,987 B1 | 4/2001 | Hirsch et al. |
| 6,221,047 B1 | 4/2001 | Greene et al. |
| 6,730,062 B2 | 5/2004 | Hoffman et al. |
| 6,916,311 B2 | 7/2005 | Vojtasek |
| 6,921,396 B1 | 7/2005 | Wilson et al. |
| 6,966,898 B1 | 11/2005 | Pouget et al. |
| 6,966,899 B2 | 11/2005 | Hochman et al. |
| 6,969,376 B2 | 11/2005 | Takagi et al. |
| 6,972,002 B2 | 12/2005 | Thorne |
| 2002/0062107 A1 | 5/2002 | Parmigiani et al. |

OTHER PUBLICATIONS

Product Brochure: "A.V. Fistula Needle Set"; JMS North America Corporation; California, USA; Undated; not admitted as prior art.

McCleary, Caldero, Adams; "Guarded Fistula Needle Reduces Needle Stick Injuries in Hemodialysis"; Nephrology News & Issues; May 2002; pp. 65-68; USA.

* cited by examiner

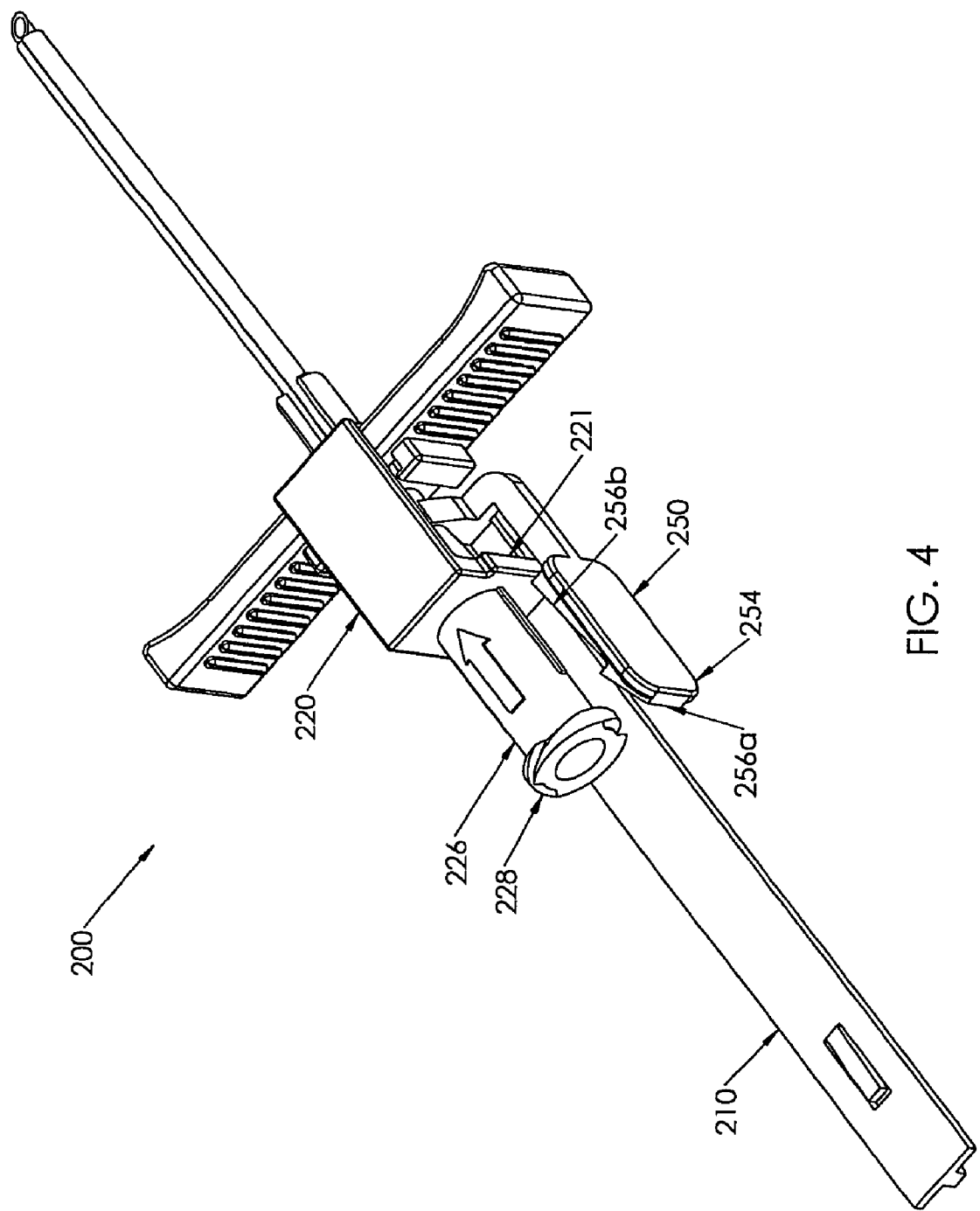

CATHETER SAFETY NEEDLE

CROSS REFERENCE TO RELATED INVENTION

The present application claims the benefit of U.S. Provisional Patent Application Ser. No. 60/548,427, filed on 26 Feb. 2004.

FIELD OF THE INVENTION

The present invention relates to a catheter insertion needle that is retractable into a safety position after use to prevent accidental sticks.

BACKGROUND OF THE INVENTION

The introduction of a device through tissue of a living body typically requires the use of a sharp instrument such as a scalpel or a needle to provide access into the tissue. For example, for the insertion of a catheter into a blood vessel a needle is used to access the vessel. The needle includes a hollow bore cannula that provides a conduit for an introducer device, such as a guide wire, to be inserted through the cannula and into the blood vessel. After insertion of the guide wire, the needle is withdrawn proximally along the guide wire and discarded. The catheter is then inserted into the vessel over the guide wire, and the guide wire is then removed.

The removal of the needle exposes the sharp insertion tip of the needle to the medical personnel inserting the catheter. This sharp tip poses a danger of a needle stick to the medical personnel. Addtionally, this tip is contaminated with the patient's blood, which leads to the danger of blood-borne pathogens, such as HIV or hepatitis, to contaminate the needle and pose a further health risk for the medical personnel administering the needle.

It would be beneficial to provide a needle that can be easily and quickly placed into a safety position after removal from the patient's blood vessel in order to minimize the chance for a needle stick.

SUMMARY OF THE INVENTION

Briefly, the present invention provides a catheter insertion needle assembly. The assembly includes a generally elongated body having a proximal end and a distal end. A needle guard is disposed at the distal end of the body in a needle guard plane. A first locking member is disposed proximate to the distal end of the body. A second locking member is disposed at the proximal end of the body. A slider assembly includes a slider body being slidably disposed on the elongated body and further including a needle having an elongated needle body extending to a distal tip, and a cannulating portion extending through the elongated needle body. The needle extends distally of the slider and through the needle guard. A first locking tab is releasably engageable with the first locking member. A second locking portion is lockably engageable with the second locking member. The first locking tab is releasable from the first locking member to allow the slider to slide between a distal position relative to the elongated body wherein the tip extends distally of the needle guard and a proximal position relative to the elongated body wherein the tip is disposed within the needle guard plane. When the slider is disposed at the proximal position, the second locking portion engages the second locking member to preclude the slider from sliding distally relative to the elongated body.

Further, the present invention provides a catheter insertion needle assembly including a generally elongated body; a needle guard disposed at the distal end of the body in a needle guard plane, and a slider assembly comprising a slider slidably disposed on the elongated body and a needle having an elongated needle body. A tip is disposed at a distal end of the elongated needle body and a cannulating portion extends through the elongated needle body. The needle extends distally of the slider and through the needle guard. A first retention section for releasably retaining the slider in a distal position relative to the elongated body and a second retention section for retaining the slider in a proximal position relative to the elongated body are also provided.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 4 is a rear perspective view of a catheter insertion needle assembly according to a second embodiment of the present invention.

DETAILED DESCRIPTION OF THE INVENTION

Figure 1:
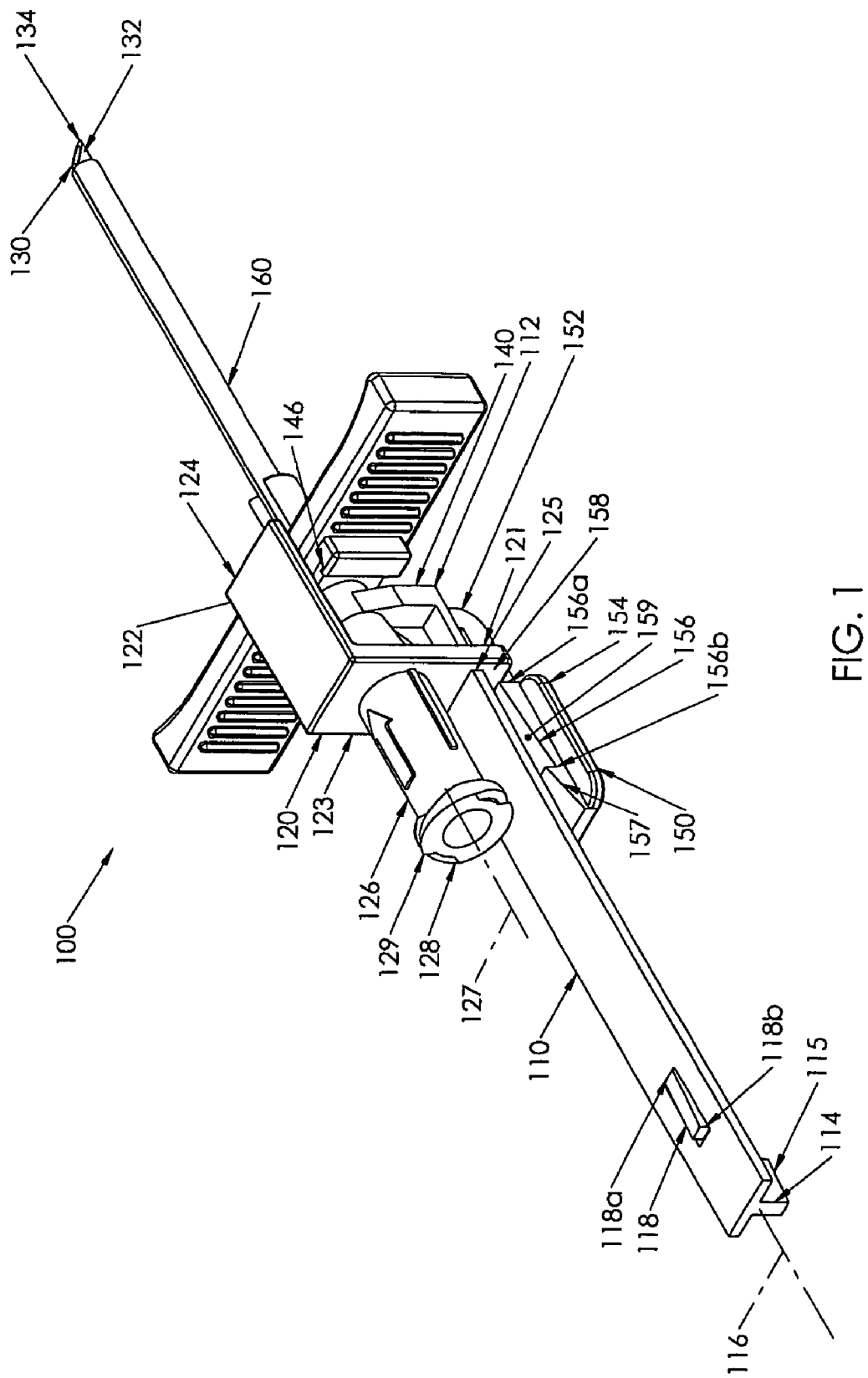
FIG. 1 is a rear perspective view of a catheter insertion needle assembly according to a first embodiment of the present invention.

In the drawings, like numerals indicate like elements throughout. Certain terminology is used herein for convenience only and is not to be taken as a limitation on the present invention. The words "proximal" and "distal" refer to directions away from and closer to, respectively, the insertion tip of the needle in the catheter insertion needle assembly according to the present invention. The terminology includes the words above specifically mentioned, derivatives thereof, and words of similar import. The following describes preferred embodiments of the invention. However, it should be understood based on this disclosure, that the invention is not limited by the preferred embodiments described herein.

Referring to FIG. 1, a perspective view of a catheter insertion needle assembly 100 according to a first embodiment of the present invention is shown. The assembly 100 includes an elongated body 110, a slider assembly 120, a needle housing 126, a needle 130, and a needle guard 140. The generally elongated body 110 has a distal end 112, a proximal end 114, and a longitudinal axis 116 extending between the distal end 112 and the proximal end 114. The body 110 also includes a proximal locking member 118 that has a distal end 118a connected to the body 110 and a proximal free end 118b that extends beyond the plane of the body 110. A positive stop 115 extends downward from the proximal end 114, away from the longitudinal axis 116.

A slider assembly 120 is slidingly disposed on the body 110 for sliding translation between the distal end 112 and the proximal end 114 of the body 110. The slider assembly 120 includes a slider body 122 that includes a vertical or first leg portion 123 and a horizontal or second leg portion 124 that extends perpendicularly from the first leg portion 123. The first leg portion 123 includes a slot 125 that is sized to allow the body 110 to be slidingly disposed therethrough. The first leg portion 123 also includes a locking tab 121 that extends below slot 125, which may simply be defined by the end of the first leg portion. The slider assembly 120 further includes a needle housing 126 that extends through the first leg portion 123 along an axis 127 generally parallel to the longitudinal axis 116. The needle housing 126 includes a proximal portion 128 defining a widened entrance to the needle proximal end and that preferably includes a male luer fitting 129 and a distal needle portion or needle 130 that includes a cannulating portion 132 with a needle tip 134. The needle tip 134 fluidly communicates with the widened proximal entrance of the male luer fitting 129 to allow fluid and/or a catheter guide wire (not shown) to be transmitted through the needle housing 126 and into the needle proximal end.

Figure 2:
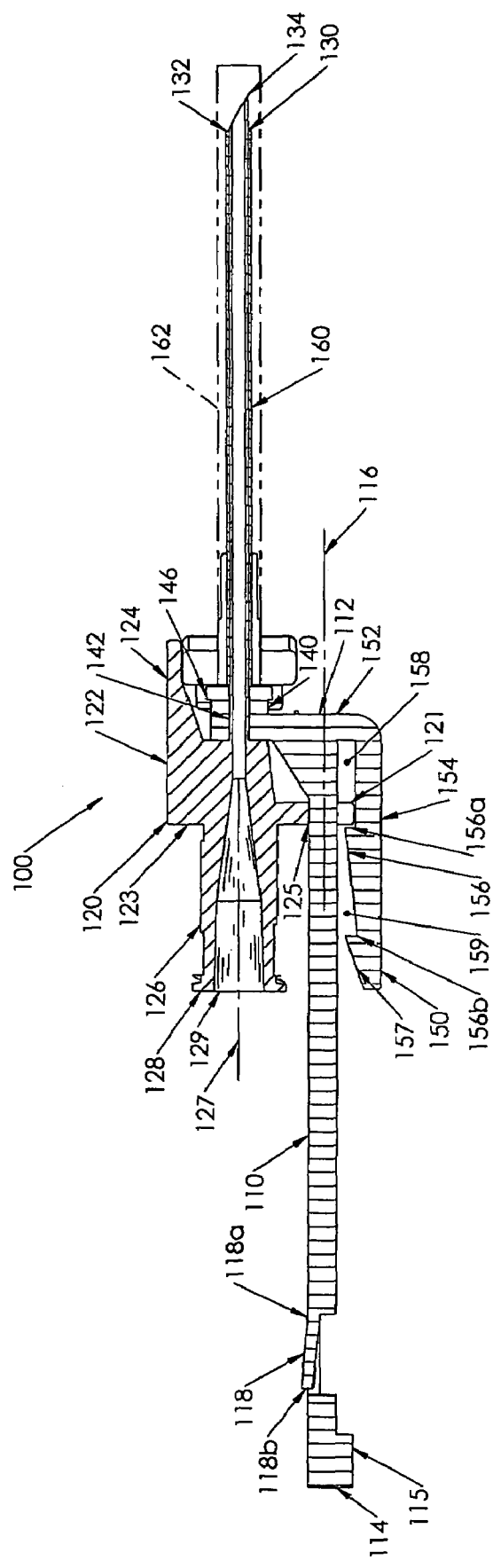
FIG. 2 is a sectional view of the catheter insertion needle assembly of FIG. 1 with a sheath shown in position in phantom.
Figure 3:
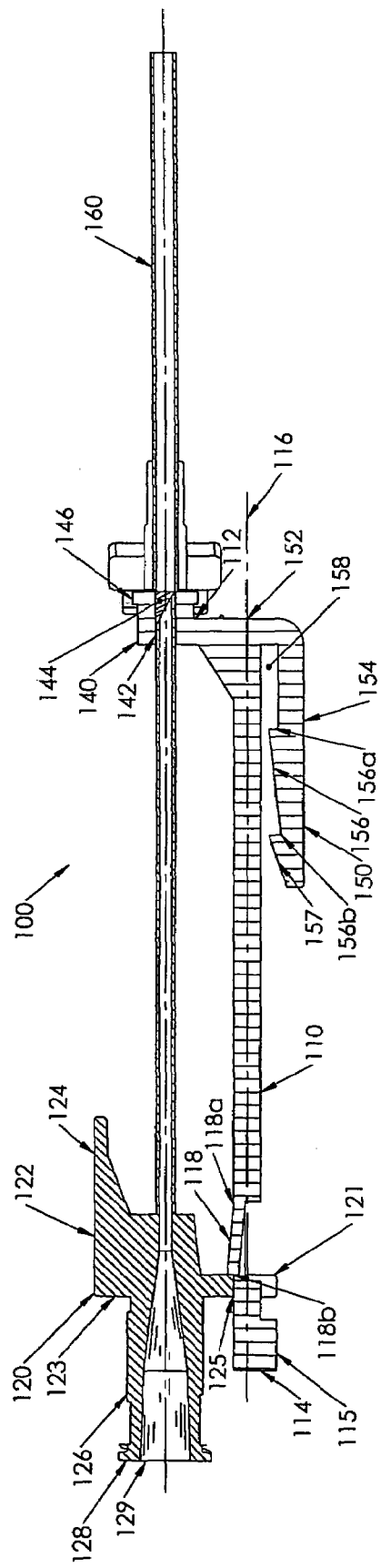
FIG. 3 is a sectional view of the catheter insertion needle assembly of FIG. 1, with the needle in a retracted position and the sheath removed.

Referring now to FIG. 2, the body 110 includes a needle guard 140 that is disposed at the distal end 112 of the body 110. The needle guard 140 extends in a plane preferably generally perpendicular to the longitudinal axis 116 of the body 110 and includes a preferably generally circular opening 142 that extends through the needle guard 140 generally parallel to the longitudinal axis 116 of the body 110. As seen in FIG. 3, a seal 144 may be disposed within the opening 142 along the plane of the needle guard 140. The seal 144 may be constructed from silicone, or from some other compatible polymer. The seal 144 serves to encapsulate the needle tip 134 after needle use, as will be described in more detail herein.

Referring back to FIG. 2, the needle guard 140 further includes a sheath retainer 146 disposed on a distal end of the needle guard 140. The sheath retainer 146 is sized and shaped to allow a needle sheath, such as the needle sheath 160, to be slidably disposed on the sheath retainer 146. Optionally, a tubular safety sheath 162 (shown in dashed lines) may be disposed over the needle sheath 160 and the cannulating portion 132 of the needle housing 126 to prevent accidental sticking prior to use.

A first locking member 150 is disposed proximate to the distal end 112 of the elongated body 110. The first locking member 150 includes a fixed portion 152 that extends away from the body 110 preferably generally perpendicularly to the longitudinal axis 116 of the body 110. A free portion 154 of the first locking member 150 extends from the fixed portion 152 generally parallel to the longitudinal axis 116 of the body 110 and toward the proximal end 114 of the body 110. The free portion 154 of the first locking member 150 preferably includes a first tapered portion 156 that tapers from a larger distal end 156a to a narrower proximal end 156b. An open space 158 is formed between the fixed portion 152 and the distal end 156a of the first tapered portion 156 that is sized to retain the locking tab 121 of the slider assembly 120. A second tapered portion 157 extends proximally from the first tapered portion 156. A detent 159 is formed between the first tapered portion 156 and the second tapered portion 157. The detent 159 allows the slider assembly 120 to be partially drawn distally so that the needle tip 134 is drawn into the needle sheath 160 prior to insertion of the needle 130 into the patient.

The free portion 154 of the first locking member 150 is able to be biased away from the body 110 to disengage the locking tab 121 of the slider assembly 120 from the free portion 154 of the first locking member 150 in order to enable the slider assembly 120 to be disposed proximally along the body 110.

Preferably, both the body 110 and the slider assembly 120 are constructed from as suitable polymer, such as polystyrene or ISOPLAST® polyurethane sold by Dow Corning of Midland, Mich. although those skilled in the art will recognize that the body 110 and the slider 120 may be constructed from other materials instead.

Initially, the slider assembly 120 is disposed toward the distal end of the body 110, such That the locking tab 121 is disposed within the open space 158, such as is shown in FIGS. 1 and 2. The free portion 156 of the first locking member 150 retains the locking tab 121 within the open space 158. In this position, the needle (130) extends distally of the body 110 and of the needle guard 140. Preferably, the sheath 160 is disposed over the cannulating portion 132 of the needle and the tubular protector 162 is disposed over the sheath 160 and the cannulating portion 132 of the needle such that the needle tip 134 of the needle is covered by the protector 162 to prevent accidental sticking by the needle.

Figure 2A:
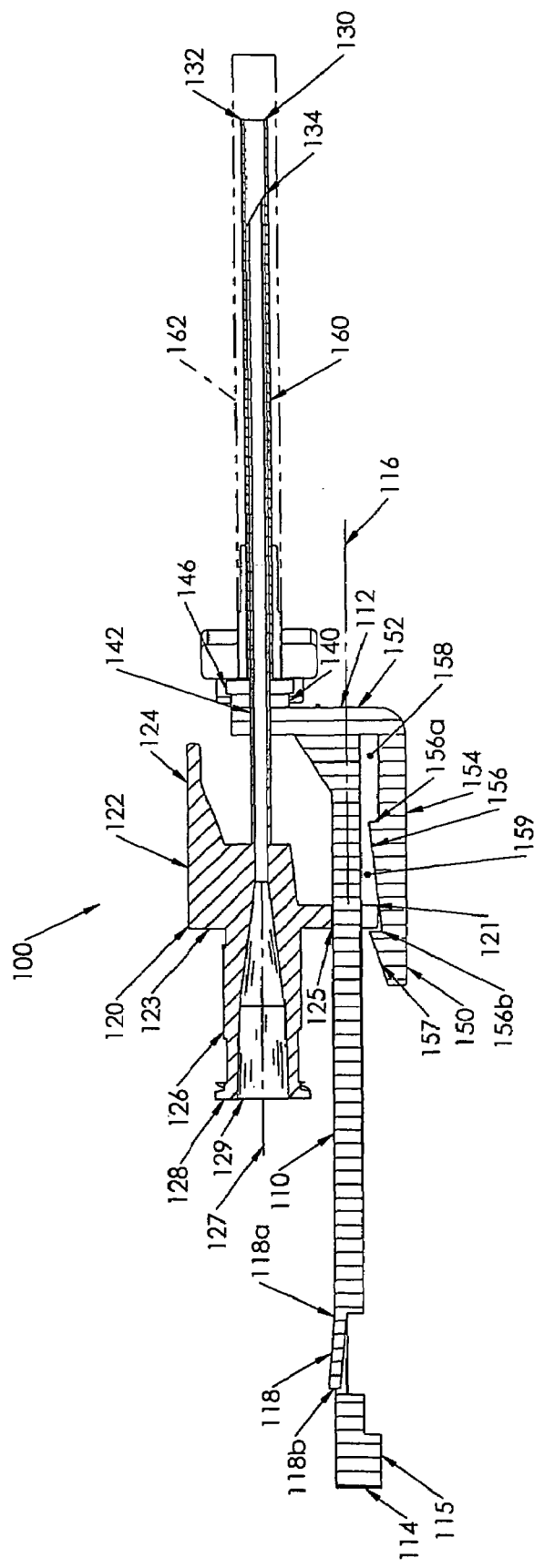
FIG. 2A is a sectional view of the catheter insertion needle assembly of FIG. 1, with the needle in a safety position retracted within the insertion sheath.

When the medical personnel is ready to administer the insertion of the needle, the medical personnel biases the free portion 154 of the first locking member 150 away from the longitudinal axis 116 of the body 110 until the distal end 156b of the first tapered portion 156 of the first locking member 150 clears the locking tab 121 of the slider assembly 120. The slider assembly 120 is then disposed proximally along the body 110 to the position shown in FIG. 2A. The locking tab 121 of the slider assembly 120 is now secured within the detent 159. The needle tip 134 of the needle 130 is now safely disposed within the needle sheath 160 and the medical personnel is not in danger of an accidental needle stick.

The tubular safety sheath 162 is then removed from the needle and the sheath 160 by sliding the tubular safety sheath 162 distally along the length of the needle until the tubular safety sheath 162 is removed therefrom. The tubular safety sheath 162 is no longer needed and may be discarded. The needle housing 126 is slid distally until the locking tab 121 locks into the open space 158, allowing the needle tip 134 to extend distally of the sheath 160. The cannulating portion 132 of the needle is then inserted into the desired location in a patient according to methods well known in the art.

When it is desired to withdraw the needle from the patient, the free portion 154 of the first locking member 150 is biased away from the longitudinal axis 116 of the body 110 until the distal end 156b of the free portion 154 of the first locking member 150 clears the locking tab 121 of the slider assembly 120. The slider assembly 120 is then disposed proximally along the body 110 to the position shown in FIG. 3, further disposing the needle 130 proximally along the body 110 as well.

As the slider assembly 120 is disposed toward the proximal end 114 of the body 110, the slider assembly 120 engages the proximal locking member 118, depressing the proximal end 118b toward the longitudinal axis 116. As the proximal locking member 118 clears the slot 125, the proximal end 118b of the proximal locking member 118 biases back to its original position, again extending out of the plane of body 110 but now distally of first leg portion 123, which now acts as a second locking portion, preventing the slider assembly 120 from being disposed distally beyond the proximal locking member 118. Preferably generally simultaneously, the distal tip 134 of the needle is disposed proximally through the sheath 160 and into the needle guard 140, where the needle guard 140 prevents a user from being accidentally stuck. If the optional seal 144 is used, the distal tip 134 of the needle assembly 126 is disposed within the seal 144 as a further safety precaution. To prevent the slider assembly 120 from being pulled off of the body 110, the stop 115 engages the locking tab 121 if the locking tab 121 is slid too far proximally along the body 110.

At this point, the distal tip 134 of the needle is fully retracted from the sheath 160, and the sheath 160 may be slidingly removed from the sheath retainer 146, by sliding the sheath 160 in a direction toward either the top or bottom of the page of FIG. 3, as is well known to those skilled in the art. The sheath 160 remains inserted into the patient, and the assembly 100 may now be disposed in a medical waste container or other suitable container.

An alternate embodiment of a catheter needle insertion assembly 200, shown in FIG. 4, is similar to the catheter needle insertion assembly 100 described above and shown in FIGS. 1-3, with the exception of the first locking member 150, which has been replaced by a first locking member 250, shown in FIG. 4. The first locking member 250 is disposed to the side of the syringe 226 such that, to release the syringe 226 from the first locking member 250, the proximal end 256*a* of the free portion 254 of the first locking member 250 is biased away from the proximal end 228 of the syringe 226 until the distal end 256*b* of the free portion 254 of the first locking member 250 clears the locking tab 221 of the slider 220. The slider 220 is then disposed proximally along the body 210, further disposing the syringe 226 proximally along the body 210 as well. The remaining operation of the assembly 200 is identical to the operation of the assembly 100 as described above.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A needle assembly for use in a catheter implantation procedure into a patient by providing for fluid injection therethrough or insertion of a guide wire therethrough into a patient, comprising:
    a generally elongated body having:
        a proximal end and a distal end;
        a needle guard disposed at the distal end of the body in a needle guard plane;
        a first locking member disposed proximate to the distal end of the body; and
        a second locking member disposed at the proximal end of the body; and
    a slider assembly including:
        a slider being slidably disposed on the body;
        a needle having an elongated needle body, a tip disposed at a distal end of the elongated needle body and a cannulating portion extending through the elongated needle body, wherein the needle extends distally of the slider and through the needle guard, and wherein a proximal end of the needle is open to receive fluid injectable thereinto or to receive insertably thereinto a guide wire;
        a first locking tab releasably engageable with the first locking member; and
        a second locking portion lockably engageable with the second locking member;
    wherein the first locking tab is releasable from the first locking member to allow the slider to slide between a distal position relative to the body wherein the tip extends distally of the needle guard and a proximal position relative to the body wherein the tip is disposed within the needle guard plane and wherein, when the slider is disposed at the proximal position, the second locking portion engages the second locking member to preclude the slider from sliding distally relative to the body, wherein the first locking member comprises a fixed portion fixedly connected to the body and a free portion movable between a locked position wherein the first locking tab is engaged with the first locking member and an unlocked position wherein the first locking tab is disengaged from the first locking member, and wherein the free portion is biased toward the locked position.

2. The needle assembly according to claim 1, wherein the slider assembly defines a widened proximal opening facilitating access to the needle proximal end.

3. The needle assembly according to claim 1, wherein the proximal end of the body further comprises a stop member to restrict travel of the slider proximally relative to the body.

4. The needle assembly according to claim 1, wherein the needle guard further comprises a polymer seal disposed within the needle guard plane.

5. The needle assembly according to claim 4, wherein when the tip is disposed within the needle guard plane, the tip is sealed within the polymer seal.

6. The needle assembly according to claim 4, wherein the polymer seal is a silicone seal.

7. The needle assembly according to claim 1, wherein the distal end of the body comprises a sheath retainer adapted to releasably retain a catheter insertion sheath having a tubular body extending therefrom.

8. The needle assembly according to claim 7, wherein the catheter insertion sheath comprises a tubular sheath body extending distally therefrom, and wherein, when the slider is in the distal position, the needle is disposed within the tubular sheath body such that the tip of the needle extends from the tubular sheath body.

9. The needle assembly according to claim 7 wherein, when the slider is in the proximal position, the catheter insertion sheath is releasable from the sheath retainer.

10. A needle assembly for insertion into a patient of a guide wire for use in catheter insertion, comprising:
    a generally elongated body having:
        a proximal end and a distal end;
        a needle guard disposed at the distal end of the body in a needle guard plane;
    a slider assembly comprising:
        a slider being slidably disposed on the body;
        a needle having an elongated needle body, a tip disposed at a distal end of the elongated needle body and a cannulating portion extending through the elongated needle body, wherein the needle extends distally of the slider and through the needle guard, and wherein a proximal end of the needle is open to receive fluid injectable thereinto or to receive insertably thereinto a guide wire;
        a first retention section for releasably retaining the slider in a distal position relative to the body; and
        a second retention section for retaining the slider in a proximal position relative to the body;
    wherein the distal end of the body comprises a sheath retainer adapted to releasably retain a catheter insertion sheath having a tubular body extending therefrom, wherein the catheter insertion sheath comprises a tubular sheath body extending distally therefrom, and wherein, when the slider is in the distal position, the needle is disposed within the tubular sheath body such that the tip of the needle extends from the tubular sheath body.

11. The needle assembly according to claim 10, wherein the slider assembly defines a widened proximal opening facilitating access to the needle proximal end.

12. The needle assembly according to claim 10, wherein the proximal end of the body further comprises a stop member to restrict travel of the slider proximally relative to the body.

13. The needle assembly according to claim 10, wherein the needle guard further comprises a polymer seal disposed within the needle guard plane.

14. The needle assembly according to claim 13, wherein when the tip is disposed within the needle guard plane, the tip is sealed within the polymer seal.

15. The needle assembly according to claim 13, wherein the polymer seal is a silicone seal.

16. The needle assembly according to claim 10 wherein, when the slider is in the proximal position, the catheter insertion sheath is releasable from the sheath retainer.

17. The needle assembly according to claim 10, wherein the first retention section is defined on a locking member extending from the elongated body, the locking member having a fixed portion fixedly connected to the body and a free portion movable between a locked position wherein the first locking tab is engaged with the first retention section where the needle tip extends beyond the tubular sheath body, and an unlocked position wherein the first locking tab is disengaged from the first retention section, and wherein the free portion is biased toward the locked position.

18. The needle assembly according to claim 8, wherein the first locking member includes a detent section defined thereon for being releasably engageable by the first locking tab of the slider assembly in an intermediate position relative to the body such that the needle tip is recessed within the tubular sheath body.

19. The needle assembly according to claim 17, wherein the assembly further includes an intermediate detent section disposed on the free portion and spaced just proximally of the first retention section for releasably retaining the slider in an intermediate position relative to the body such that the needle tip is recessed within the tubular sheath body.

* * * * *